(12) United States Patent
Otterbeck et al.

(10) Patent No.: US 8,956,647 B2
(45) Date of Patent: *Feb. 17, 2015

(54) PELLET FORMULATION FOR THE TREATMENT OF THE INTESTINAL TRACT

(71) Applicants: Norbert Otterbeck, Uberlingen (DE); Peter Gruber, Merzhausen (DE)

(72) Inventors: Norbert Otterbeck, Uberlingen (DE); Peter Gruber, Merzhausen (DE)

(73) Assignee: Dr. Falk Pharma GmbH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/951,951

(22) Filed: Jul. 26, 2013

(65) Prior Publication Data

US 2013/0309311 A1 Nov. 21, 2013

Related U.S. Application Data

(60) Continuation of application No. 13/586,585, filed on Aug. 15, 2012, now Pat. No. 8,496,965, which is a continuation of application No. 12/236,157, filed on Sep. 23, 2008, now Pat. No. 8,337,886, which is a (Continued)

(51) Int. Cl.
*A61K 9/52* (2006.01)
*A61K 9/00* (2006.01)
*A61K 9/16* (2006.01)
*A61K 9/50* (2006.01)

(Continued)

(52) U.S. Cl.
CPC ............ *A61K 9/0053* (2013.01); *A61K 9/1635* (2013.01); *A61K 9/1652* (2013.01); *A61K 9/501* (2013.01); *A61K 9/5026* (2013.01); *A61K 9/5042* (2013.01); *A61K 31/60* (2013.01); *A61K 9/16* (2013.01); *A61K 9/141* (2013.01); *A61K 31/606* (2013.01)
USPC .......................................................... 424/457

(58) Field of Classification Search
CPC . A61K 9/0053; A61K 9/1635; A61K 9/1652; A61K 9/501; A61K 9/5026; A61K 9/5042; A61K 31/60; A61K 9/16; A61K 9/141; A61K 31/606
USPC ................................................. 424/457, 474
See application file for complete search history.

(56) References Cited

U.S. PATENT DOCUMENTS 2,738,303 A 3/1956 Blythe
2,897,121 A 7/1959 Wagner (Continued)

FOREIGN PATENT DOCUMENTS

CA 1336070 C 6/1995
DE 4236025 A1 4/1994

(Continued)

OTHER PUBLICATIONS

"U.S. Appl. No. 10/360,410, Final Office Action mailed Dec. 6, 2007", FOAR, 8 pgs.

(Continued)

*Primary Examiner* — San-Ming Hui
(74) *Attorney, Agent, or Firm* — McCarter & English LLP; Jonathan M. Sparks; Michael J. DeGrazia

(57) ABSTRACT

An orally administrable pharmaceutical pellet formulation for the treatment of the intestinal tract is disclosed, which comprises a core and an enteric coating, the core including, as a pharmaceutical active compound, aminosalicylic acid or a pharmaceutically tolerable salt or a derivative thereof.

49 Claims, 2 Drawing Sheets

Figure 1:
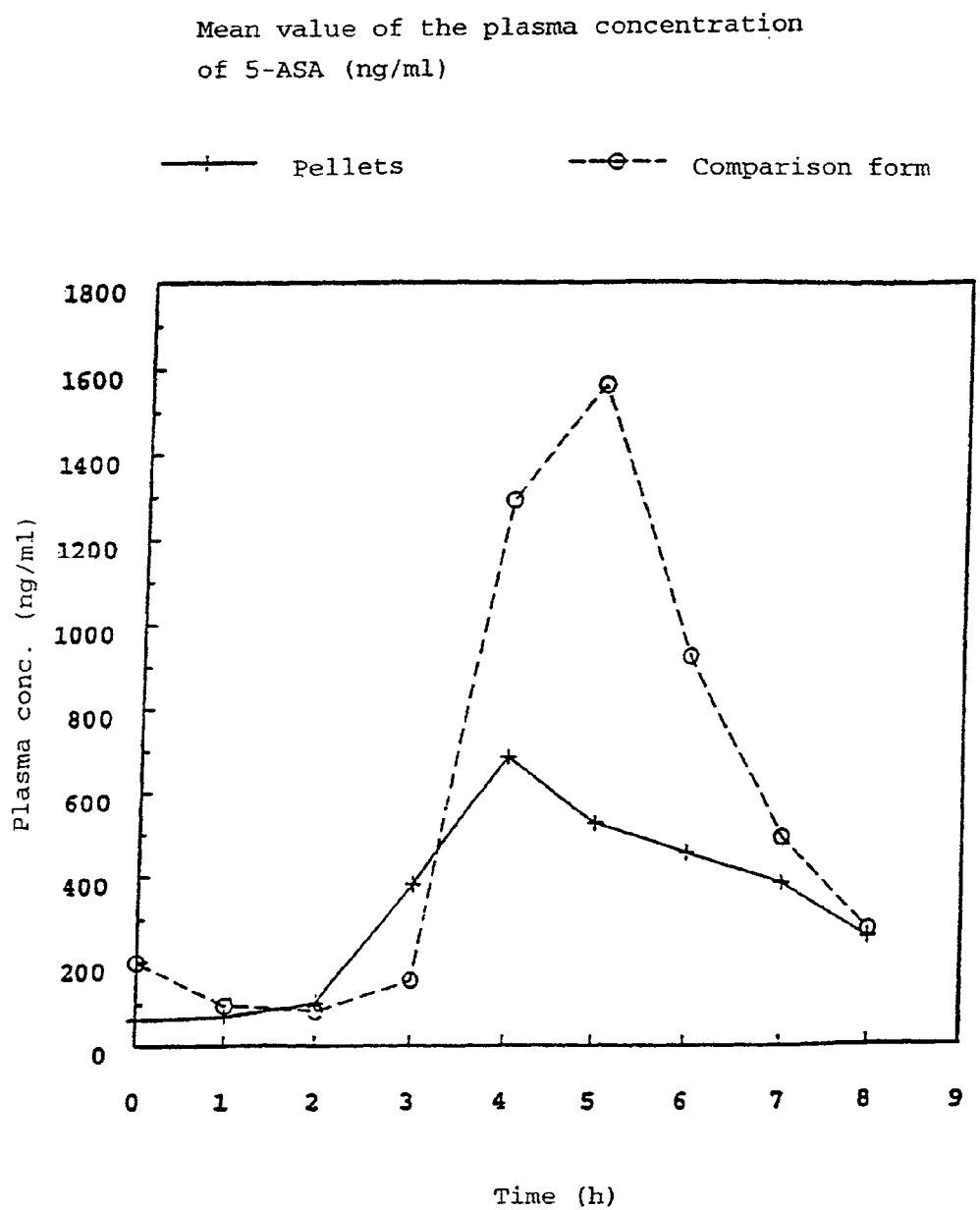

Related U.S. Application Data continuation of application No. 10/360,410, filed on Feb. 7, 2003, now Pat. No. 7,547,451, which is a division of application No. 09/906,494, filed on Jul. 16, 2001, now Pat. No. 6,551,620, which is a continuation of application No. 09/194,213, filed as application No. PCT/EP98/02319 on Apr. 20, 1998, now Pat. No. 6,277,412.

(51) Int. Cl.
  *A61K 31/60* (2006.01)
  *A61K 9/14* (2006.01)
  *A61K 31/606* (2006.01)

(56) References Cited

U.S. PATENT DOCUMENTS

| | | | |
|---|---|---|---|
| 2,987,445 A | 6/1961 | Levesque |
| 3,087,860 A | 4/1963 | Endicott |
| 3,835,221 A | 9/1974 | Fulberth et al. |
| 3,938,515 A | 2/1976 | Leeper et al. |
| 4,138,475 A | 2/1979 | McAinsh et al. |
| 4,432,966 A | 2/1984 | Zeitoun et al. |
| 4,496,553 A | 1/1985 | Halskov |
| 4,540,685 A | 9/1985 | Bauer |
| 4,632,921 A | 12/1986 | Bauer |
| 4,668,517 A | 5/1987 | Weber et al. |
| 4,688,517 A | 8/1987 | Hollman |
| 4,699,902 A | 10/1987 | Bauer |
| 4,780,318 A | 10/1988 | Appelgren et al. |
| 4,863,744 A | 9/1989 | Urquhart et al. |
| 4,985,418 A | 1/1991 | Richards |
| 5,009,897 A | 4/1991 | Brinker et al. |
| 5,096,717 A | 3/1992 | Wirth et al. |
| 5,171,580 A | 12/1992 | Iamartino et al. |
| 5,178,866 A | 1/1993 | Wright et al. |
| 5,217,720 A | 6/1993 | Sekigawa et al. |
| 5,316,772 A | 5/1994 | Jurgens, Jr. et al. |
| 5,401,512 A | 3/1995 | Rhodes et al. |
| 5,472,710 A | 12/1995 | Klokkers-Bethke et al. |
| 5,505,966 A | 4/1996 | Edman et al. |
| 5,536,507 A | 7/1996 | Abramowitz et al. |
| 5,541,170 A | 7/1996 | Rhodes et al. |
| 5,541,171 A | 7/1996 | Rhodes et al. |
| 5,643,602 A | 7/1997 | Ulmius |
| 5,656,294 A | 8/1997 | Friend et al. |
| 5,879,705 A | 3/1999 | Heafield et al. |
| 5,945,124 A | 8/1999 | Sachs et al. |
| 6,004,581 A | 12/1999 | Jepsen et al. |
| 6,277,412 B1 | 8/2001 | Otterbeck |
| 6,423,340 B1 | 7/2002 | Ulmius |
| 6,551,620 B2 | 4/2003 | Otterbeck |
| 7,547,451 B2 | 6/2009 | Otterbeck |
| 8,337,886 B2 | 12/2012 | Otterbeck |
| 8,496,965 B2 | 7/2013 | Otterbeck |

FOREIGN PATENT DOCUMENTS

| | | | |
|---|---|---|---|
| DE | 19732 903 A1 | 2/1999 |
| EP | 006200 A1 | 1/1980 |
| EP | 0040590 A2 | 11/1981 |
| EP | 0148811 A1 | 7/1985 |
| EP | 0248447 A2 | 12/1987 |
| EP | 0278174 A2 | 8/1988 |
| EP | 0308665 A2 | 3/1989 |
| EP | 0377477 A1 | 7/1990 |
| EP | 0453001 A1 | 10/1991 |
| EP | 0485840 A2 | 5/1992 |
| EP | 0572486 A1 | 12/1993 |
| EP | 0595110 A1 | 5/1994 |
| EP | 0629398 A1 | 12/1994 |
| EP | 0636370 A1 | 2/1995 |
| EP | 0671168 A1 | 9/1995 |
| EP | 0673645 A2 | 9/1995 |
| EP | 0759303 A1 | 2/1997 |
| FR | 2692484 A1 | 12/1993 |
| GB | 0 219 026 A | 6/1925 |
| GB | 1219026 A | 1/1971 |
| WO | 83/00435 A1 | 2/1983 |
| WO | 87/01588 A1 | 3/1987 |
| WO | 91/07949 A1 | 6/1991 |
| WO | 92/14452 A1 | 9/1992 |
| WO | 9216206 A1 | 10/1992 |
| WO | 93/07859 A1 | 4/1993 |
| WO | 95/16451 A1 | 6/1995 |
| WO | 95/18622 A1 | 7/1995 |
| WO | 95/35100 A1 | 12/1995 |
| WO | 96/04918 A1 | 2/1996 |
| WO | 96/29058 A1 | 9/1996 |
| WO | 96/31202 A1 | 10/1996 |
| WO | 97/23199 A1 | 7/1997 |

OTHER PUBLICATIONS

"U.S. Appl. No. 10/360,410, Response filed Jun. 6, 2008 to Final Office Action mailed Dec. 6, 2007" 6 pgs.

"U.S. Appl. No. 10/360,410 Notice of Allowance mailed Jul. 11, 2008", NOAR, 7 pgs.

"Data Sheets for Registration", Rohm Brochure, Pharma Polymers, 4 pages. 2001.

"Dictionary Entries: 'Mesalamine,' 'Proctosigmoiditis' and 'Inflammation'", Stedman's Medical Dictionary, Obtained from the Physician's DeskReference Electronic Library on the World Wide Web at http://www.pdrel.com/>, on Dec. 17, 1999, 5 p., (1999).

"Dictionary Entry: 'Pentasa Capsules' (Mesalamine/5-aminosalicylic Acid)", Physician's Desk Reference, Obtained from the Physician's Desk Reference Electronic Library on the World Wide Web at http://www.pdrel.com/>, on Dec. 17, 1999, 8 p.,(1999).

"U.S. Appl. No. 09/194,213 Final Office Action mailed Sep. 26, 2000", 7 pgs.

"U.S. Appl. No. 09/194,213 Non Final Office Action mailed Dec. 28, 1999", 7 pgs.

"U.S. Appl. No. 09/194,213 Notice of Allowance mailed Mar. 30, 2001", 5 pgs.

"U.S. Appl. No. 09/194,213 Preliminary Amendment filed Nov. 20, 1998", 2 pgs.

"U.S. Appl. No. 09/194,213 Response filed Jun. 28, 2000 to Non Final Office Action mailed Dec. 28, 1999", 5 pgs.

"U.S. Appl. No. 09/194,213 Response filed Mar. 14, 2001 to Final Office Action mailed Sep. 26, 2000", 5 pgs.

"U.S. Appl. No. 09/906,494 Non Final Office Action mailed May 6, 2002", 7 pgs.

"U.S. Appl. No. 09/906,494 Non Final Office Action mailed Sep. 25, 2001", 7 pgs.

"U.S. Appl. No. 09/906,494 Notice of Allowance mailed Nov. 4, 2002", 5 pgs.

"U.S. Appl. No. 09/906,494 Preliminary Amendment filed Jul. 18, 2001", 4 pgs.

"U.S. Appl. No. 09/906,494 Response filed Aug. 6, 2002 to Non Final Office Action mailed May 6, 2002", 7 pgs.

"U.S. Appl. No. 09/906,494 Response filed Dec. 28, 2001 to Non Final Office Action mailed Sep. 25, 2001", 7 pgs.

"U.S. Appl. No. 10/360,410, Response filed Sep. 27, 2007 to Non-Final Office Action mailed May 31, 2007", 7.

Badawi, A.A., et al., "Drug Release From Matrices Made of Polymers With Reacting Sites", International Journal of Pharmaceutics, 6, 55-62, (1980).

Barry, M., "Selected side-effects: 9. Mesalazine and renal impairment", Prescriber's Journal, vol. 32, No. 5, pp. 205-209, (1992).

J. Healey, Gastrointestinal Transit and Release of Mesalazine Tablets in Patients with Inflammatory Bowel Disease, 25 Scand J. Gastroenterology 47 (Supp. 127 1990).

Lin, S.Y., et al., "Calcium Alginate Beads as Core Carriers of 5-Aminosalicylic Acid", Pharmaceutical Research, 9(9), 1128-1131, (1992).

Polymethacrylates, in Handbook of Pharmaceutical Excipients 362 (Ainley Wade & Paul 1. Weller eds., 2d ed. 1994).

(56) References Cited

OTHER PUBLICATIONS

Watts, P.J., et al., "Encapsulation of 5-aminosalicylic Acid into Eudragit RS Microspheres and Modulation of their Release Characteristics by Use of Surfactants", Journal of Controlled Release, 16, 311-318, (1991).

*Salix Pharmaceuticals, Inc. and Dr. Falk Pharma GmbH v. Lupon Limited and Lupin Pharmaceuticals, Inc.*, "Order Construing the Terms of U.S. Patent Nos. 6,551,620; 7,547,451; 8,337,886; and 8,496,965" Civil Action No. 12-1104-GMS, Document 118, filed Dec. 17, 2013.

D.K. Yu, et al., "Pharmacokinetics of 5-aminosalicylic Acid from Controlled-Release Capsules in Man," 48:273-277, European J. Clinical Pharmacology, (1995).

Peter H. Layer, et al., "Delivery and Fate of Oral Mesalamine Microgranules Within the Human Small Intestine," 108, Gastroenterology, 1427 (1995).

L.M.L. Stolk, et al., Dissolution Profiles of Mesalazine Formulations In Vitro, 12, Pharmaceutisch Weekblad Scientific Edition, 200, (1990).

Pentasa®, in Physicians' Desk Reference® 1527 (50d ed. 1996) ("PDR").

Stephen Hanauer, et al., "Mesalamine Capsules for Treatment of Active Ulcerative Colitis: Results of a Controlled Trial," 88, Americal J. Gastroenterology 1188, 1993.

U. Klotz, et al., A New Slow-Release Form of 5-Aminosalicylic Acid for the Oral Treatment of Inflammatory Bowel Disease, 35 Drug Research, 636 (1985).

K. Lehmann & D. Dreher, "Coating of Tablets and Small Particles with Acrylic Resins by Fluid Bed Technology," 2, Int'l J. Pharmaceutical Technology & Product Manufacture, 31 (1981).

Gwen M. Jantzen & Joseph R. Robinson, "Sustained- and Controlled-Release Drug Delivery Systems," 72 Modern Pharmaceutics, 575 (Gilbert S. Banker and Christopher T. Rhodes eds., 3d ed. 1996).

Masalazine, in "2 Therapeutic Drugs M70" (Sir Colin Dollery ed., 2 Vol., 1991).

Stempel, Edward, "Prolonged Drug Action," in Husa's Pharmaceutical Dispensing, 464 (Eric W. Martin & John E. Hoover eds., 6th ed. 1996).

Clive G. Wilson, et al., "Colonic Drug Delivery & Enteric Coating for Colonic Delivery," in Modified-Release Drug Delivery Technology, 217, (Michael J. Rathbone, et al., eds., 2003).

Guidance for Industry, "SUPAC-MR: Modified Resealse Solid Oral Dosage Forms," Food and Drug Administration, Sep. 1997, at 34.

S.S. Davis, "The Design and Evaluation of Controlled Release Systems for the Gastrointestinal Tract," 2, J. Controlled Release, 27 (1985).

"Mesalazine," Martindale: The Complete Drug Reference, pp. 1199-1200, Kathleen Parfitt ed., 32d ed., 1999.

Ghebre-Sellassie, Isaac, et al., "Pharmaceutical Pelletization Technology," Drugs and the Pharmaceutical Sciences, vol. 37, 287 pages, 1989.

Drug Release. (1990). In USP XXII: The United States Pharmacopeia (36th ed., pp. 1580-1583).

Dukic-Ott, A., et al., "Production of pellets via extrusion-spheronisation without the incorporation of microcrystalline cellulose: A critical review." European Journal of Pharmaceutics and Biopharmaceutics 71: 38-46 (2009).

EC-Naprosyn®/ Naprosyn®/ Anaprox®/Anaprox® DS / Naprosyn® product insert.

Efentakis, M. et al, "Dimensional changes, gel layer evolution and drug release studies in hydrophilic matrices." Int J Pharm 339: 66-75 (2007).

Erkoboni, David F., Extrusion-Spheronization as a Granulation Technique in Handbook of Pharmaceutical Granulation Technology 333-368 (Parikh ed., 1997).

Erythromycin. (1996). In The Merck Index (12 ed. pp. 3720-3721).

Erythromycin. (1999). In Therapeutic Drugs, 1: E50-54 (Dollery ed.).

Evans, D.F. et al., "Measurement of gastrointestinal pH profiles in normal ambulant human subjects." Gut 29:1035-1041 (1988).

FDA Approval Package for Pentasa Capsules (1993).

Feagan, B., "Oral 5-aminosalicylic maintenance of remission in ulcerative colitis (review)." The Cochrane Collaboration (2012).

Feagan, B.G. et al., "Are There Any Differences in the Efficacy and Safety of Different Formulations of Oral 5-ASA Used for Induction and Maintenance of Remission in Ulcerative Colitis? Evidence from Cochrane Reviews." Inflammatory Bowel Disease 19:2031-2040 (2013).

Fielden, K., et al., "Extrusion and Extruders" in Pharmaceutical Technology 5 (1992).

File History for US Patent No. 6,551,620, 2014.
File History for US Patent No. 7,547,451, 2014.
File History for US Patent No. 8,337,886, 2014.
File History for US Patent No. 8,496,965, 2014.

FIP Guidelines for Dissolution Testing of Solid Oral Products, Pharm Ind 57:362-369 (1995).

Food and Drug Administration. Guidance for Industry, SUPAC-MR: Modified Release Solid Oral Dosage Forms. Food and Drug Administration, Rockville, Md., Sep. 1997.

French, D., et al., "Evaluation of the Physicochemical Properties and Dissolution Characteristics of Mesalamine: Relevance to Controlled Intestinal Drug Delivery," Pharmaceutical Research 10:1285-1290 (1993).

Friedman, G., "Sulfasalazine and New Analogues," The American Journal of Gastroenterology 81:141-144 (1986).

Friend, D., "Colon-specific drug delivery" Advanced Drug Delivery Reviews 7:149-199 (1991).

Furazolidone. see www.Drugbank.ca/drugs/DB00614, 2014.

Galeone, M. et al., "In vivo demonstration of delivery mechanisms from sustained-release pellets." Current Therapeutic Research 29:217-234 (1981).

Galichet, "Cellulose, Microcrystalline." In Handbook of Pharmaceutical Excipients 132 (5th Ed. 2006).

Ganji, F. et al., "Theoretical description of hydrogel swelling: A review." Iranian Polymer Journal 19:375-398 (2010).

Gardner, DJ et al., "Adhesion and Surface Issues in Cellulose and Nanocellulose." J Adhesion Sci Technol 22:545-567 (2008).

Ghebre-Sellassie, I., Chapter 1: Pellets: A General Overview, Pharmaceutical Pelletization Technology 1-13 (1989).

Ghebre-Sellassie, I., Chapter 10: Formulation Variables, Pharmaceutical Pelletization Technology 217-239 (1989).

Ghebre-Sellassie, I., Chapter 2: Conventional and Specialized Coating Pans, Pharmaceutical Pelletization Technology 15-38 (1989).

Ghebre-Sellassie, I., Chapter 4: Extrusion and Spheronization Equipment, Pharmaceutical Pelletization Technology 71-100 (1989).

Ghebre-Sellassie, I., Chapter 7: Solution and Suspension Layering. Pharmaceutical Pelletization Technology 145-164 (1989).

Ghebre-Sellassie, I., Chapter 9: Extrusion and Spheronization Technology, Pharmaceutical Pelletization Technology 187-216 (1989).

Grillet, A., et al., Polymer Gel Rheology and Adhesion. Rheology, Dr. Juan De Vicente (Ed.), ISBN: 978-953-51-0187-1. 2012.

Gruber, P., et al., "Some biological issues in oral, controlled drug delivery." Adv. Drug. Del. Rev. 1:1-18 (1987).

Guimaraes, M., et al., "Does Material Matter?" Endovascular Today 70-74 (2013).

Gulrez, S., et al., "Hydrogels: Methods of preparation, characterization and applications." In Progress in Molecular and Environmental Bioengineering—From Analysis and Modeling to Technology Applications 117-150 (2011).

Gurgel, L., et al.,Characterization of depolymerized residues from extremely low acid hydrolysis (ELA) of sugarcane bagasse cellulose: Effects of degree of polymerization, cystallinity and crystallize site on thermal decomposition. Ind. Crops Prod. 36: 560-571 (2012).

Guy, A., "Cellulose, Microcrystalline" in Handbook of Pharmaceutical Excipients 129-133 (6th Ed.).

Hadgraft, J., et al., "Drug Release from Pluronic Gels," 34 (Supp) J. Pharm. Pharmacol. 3P (1982).

Hapgood K.P. & S. Obara, Hydroxypropyl Cellulose, Low-Substituted, in Handbook 6th Ed. 322.

Harwood, R., "Hypermellose," in Handbook of Pharmaceutical Excipients (5th Ed. 346-349) (2006).

Healey, J., Enteric Coatings and Delayed Release in Drug Delivery to the Gastrointestinal Tract 83-96 (Hardy ed. 1989).

(56) References Cited

OTHER PUBLICATIONS

Hoare, T. & Kohane, D., "Hydrogels in drug delivery: Progress and challenges," Polymer 49:1993-2007 (2008).

Hogan, J., "Some formulation factors involved in Hydroxypropyl Methylcellulose Controlled Release; Matrices," Excipients and delivery systems for pharmaceutical formulations—The Royal Society of Chemistry, pp. 186-190, 1995.

Hogan, J.E., "Hydroxypropylmethylcellulose sustained release technology," Drug Dev. Ind. Pharm. 15:975-99 (1989).

http://eudragit.evonik.com/ product/eudragit/en/products-services/eudragit-products/enteric-formulations/I-100/Pages/default.aspx.

http://eudragit.evonik.com/product/eudragit/en/products-services/eudragit-products/sustained-release-formulations/Pages/default.aspx [downloaded Apr. 2, 2014].

http://www.fmcbiopolymer.com/Food/Ingredients/CelluloseGel.Introduction.aspx.

http://www.ibdcare.co.uk/controversy/in-ulcerative-colitis.htm [downloaded Mar. 6, 2014].

Hydrocolloids: MCC, Hawkins Watts, http://www.hawkinswatts.com/prod_stabs9.htm.

Peppas, N., et al., "Hydrogels in Pharmaceutical Formulations," Eur. J. Pharmaceutics Biopharmaceutics 50:27-46 (2000).

Peppas, N., et al., "A Simple Equation for Description of Solute Release I. Fickian and Non-Fickian Release from Non-Swellable Devices in the Form of Slabs, Spheres, Cylinders or Discs," J. Control Release 5:23-36 (1987).

Peppas, N., "Analysis of Fickian & Non-Fickian Drug Release from Polymers," Pharmaceutica Acta Helvetiae 60:110-111 (1985).

Poloxamer. (1994). In Handbook of Pharmaceutical Excipeints (2nd Wade ed., pp. 352-354).

Porter, Stuart C., Key Factors in the Development of Modified-Release Pellets in Multiparticulate Oral Drug Delivery 217-284 (Ghebre-Sellassie ed. 1994).

Principles and Practice of Pharmaceutics. (1994). In The Pharmaceutical Codex (12th Ed., pp. 212-214).

Propranolol (hydrochloride). (1999). In Therapeutic Drugs, vol. 2: p. 259-264 (Dollery ed.).

Pygall, S. "Detailed microscopic visualization of hydration and swelling in a rapidly hydrating particle bed containing a cellulose ether," Gyms and Stabilizers for the Food Industry 14:41-46 (2008).

Rahman, M., et al, "Formulation and evaluation of Ranolazine sustained release matrix tablets using Eudragit and HPMC," Int J Pharm Biomed Res 2(1):7-12 (2011).

Rasmussen, S. et al., "5-Aminosalicylic Acid in a Slow-Release Preparation: Bioavailability, Plasma Level, and Excretion in Humans," Gastroenterology 83:1062-1070 (1982).

Reynolds, T., et al. "Polymer erosion and drug release characterization of hydroxypropyl methylcellulose matrices," Journal of Pharmaceutical Sciences 87(9):1115-1123 (1998).

Riley, S., et. al., "Tests of Renal Function in Patients with Quiescent Colitis: Effects of Drug Treatment," Gut 33(10):1348-1352 (1992).

Ritger, P. & Peppas, N., "A Simple Equation for Description of Solute Release II. Fickian and Anomalous Release from Swellable Devices," J Control Release 5:37-42 (1987).

Rosiak, Janusz M. & Yoshii, Fumio, "Hydrogels and Their Medical Applications" Nuclear Instruments and Methods in Physics Res. 151:B 56 (1999).

Rubenstein, A. et al., "Gastrointestinal-physiological variables affecting the performance of oral sustained release dosage forms," in Oral Sustained Release Formulations: Design and Evaluation (Yacobi and Halperin-Walega Eds.) 125-156, (1988).

Safdi, Alan et al., Determination of 5-ASA in Whole or Partial Mesalamine Delayed-Release Tablets Recovered From Fecal Samples of Healthy Volunteers: Do 5-ASA Delivery Systems Matter in the Treatment of Ulcerative Colitis?, presented at American College of Gastroenterology Meeting (Oct. 28-Nov. 1, 2005).

Sandborn, W.J., et al., "Once-Daily Dosing of Delayed-Release Oral Mesalamine (400-mg Tablet) Is an Effective as Twice-Daily Dosing for Maintenance of Remission of Ulcerative Colitis," Gastroenterology, 138:1286-1296 (2010).

Shale, M.J. et al., "Studies of compliance and delayed-release mesalazine therapy in patients with inflammatory bowel disease," Alimentary Pharmacology & Therapeutics 18:191-198 (2003).

Siepmann, J. & Peppas,N., "Higuchi Equation: Derivation, Applications, use and Misuse," Int'l J. Pharm. 416:6-12 (2011).

Siepmann, J. & Siepmann, F., "Mathematical Modeling of Drug Delivery," Int J Pharm 364:328-343 (2008).

Siepmann, J., et al., "Modeling of drug release from delivery systems based on the hydroxypropyl methylcellulose," Advanced Drug Delivery Reviews 48:139-157 (2001).

Silva, S., et al., "Aggregation and gelation in hydroxypropylmethyl cellulose aqueous solutions," Journal of Colloid and Interface Science, 327:333-340 (2008).

Singh, B., "Modified-Release Solid Formulations for Colonic Delivery," Recent Patents on Drug Delivery & Formulation I:53-63 (2007).

Sinha, A., et al., "Intestinal Performance of Two Mesalamine Formulations in Patients with Active Ulcerative Colitis as Assessed by Gamma Scintigraphy," Practical Gastroenterology pp. 56-69 (2003).

Tahara, K., et al, "Overall mechanism behind matrix sustained-release (SR) tablets prepared with hydroxypropyl methylcellulose 2910," J. Controlled Release 35:59-66 (1995).

Tiwari, S., et al, Modulation of drug release from hydrophilic matrices. Advancing process Solutions—Pharmaceutical Technology. Sep. 2008.

Topcare Lansoprazole PI (capsule delayed release), 2014.

Travis, S., et al., "Optimum dose of olsalazine for maintaining remission in ulcerative colitis," Gut 35:12821286 (1994).

Tu, J., et al., "Polymers in Oral Modified Release Systems," in Oral Controlled Release Formulation Design and Drug Delivery: Theory to Practice (ed. H. Wen, K. Park, Wiley, NY, p. 81, accessed on line Feb. 2014).

Tukaram, B., et.al., "The Effects of Lactose, Microcrystalline Cellulose and Dicalcium Phosphate on Swelling and Erosion of Compressed HPMC Matrix Tablets: Texture Analyzer," Iran J Pharm Res 9(4):349-358 (2010).

U.S. Pharmacopeial Convention, Section 1151 Pharmaceutical Dosage Forms, in USP 36-NF 31 854,861 (2014).

van Hees, P., et al., "Compliance to therapy in patients on a maintenance dose of sulfasalazine," Journal of Clinical Gastroenterology 4(4):333-336 (1982).

Wadworth, A. & Fitton, A., "Olsalazine: A Review of its Pharmacodynamic and Pharmacokinetic Properties, and Therapeutic Potential in Inflammatory Bowel Disease," Drug 41:647-664 (1991).

Wang, Pao-Li, et al., "Thermal-induced denaturation of two model proteins: effect of poloxamer 407 on solution stability," Int'l J. of Pharmaceutics 96:41-49 (1993).

Washington, Nina et al., "Drug Delivery to the Large Intestine and Rectum," Physiological Pharmaceutics, Barriers to Drug Absorption pp. 144-180 (2d ed. 2001).

Watts, P., et al., "Colonic Drug Delivery," Drug Dev & Indus Pharm. 23(9):893-913 (1997).

Wilding, I., et al., "Targeting of Drugs and Vaccines to the Gut," Pharmac. Ther. 62:97-124 (1994).

Wilks, Samuel & Moxon, Walter, "Lectures on Pathological Anatomy." https://archive.org/stream/lecturesonpatho00moxogoog#page/n431/mode/2up 1875, pp. 408-409.

Hypromellose. (2009). In Handbook of Pharmaceutical Excipients (Rowe et al. eds., 6th ed. pp. 326-329).

Jantzen, G. & Robinson, J., "Sustained and controlled-release drug delivery systems." Modern Pharmaceutics, 3rd Ed. 1995.

John, V., et al., "Gastrointestinal Transit of Oros Drug Delivery Systems in Healthy Volunteers: A Short Report," Brit. J. Clinical Pharmacology 19:203S-206S (1985).

Joshi, S., "Sol-Gel Behavior of Hydroxypropyl Methylcellulose (HPMC) in Ionic Media Including Drug Release," Materials 4:1861-1905 (2011).

Kabir, M.A. & J.P. Reo, "Hydroxypropyl Cellulose," in Handbook 6th Ed. 317-322.

Kadiyala, I. et al., "The study of marketed and experimental formulation approaches enabling site-specific delivery of mesalamine in patients with inflammatory bowel disease," Recent patents on drug delivery & Formulation 7:1-9 (2013).

(56) References Cited

OTHER PUBLICATIONS

Kakoulides, E., et al., "Azocrosslinked poly(acrylic acid) for colonic delivery and adhesion specificity: in vitro degradation and preliminary ex vivo bioadhesion studies," J. Controlled Release 54:95-109 (1998).
Kane, S., et al., "Medication Nonadherance and the Outcomes of Patients with Quiescent Ulcerative Colitis," The American Journal of Medicine 114:39-43 (2003).
Karbach, V., et al., "Extent of Drug Compliance in Crohn Disease Patients—Study of a Special Ambulatory Care Unit of a University Clinic" Gastroenterol 22:573-579 (1984).
Kiefer, E., "Medical management of chronic ulcerative colitis," Lahey Clinic Bulletin 12:236-241 (1962).
Khan, A., et al., "Oral Disopyramide for the Prevention of Arrhythmias in Patients with Acute Myocardial Infarction with Admitted to Open Wards," Lancet 2:892-895 (1977).
Kinget, R., et al., "Review Article: Colonic Drug Targeting," J. of Drug Targeting 6:129-149 (1998).
Kocherbitov, V., et al, "Hydration of microcrystalline cellulose and milled cellulose studied by sorption calorimetry," J. Phys Chem B. 112(12):3728-3734 (2008).
Korsmeyer, R., et al., "Mechanisms of Potassium Chloride Release from Compressed, Hydrophilic, Polymeric Matrices: Effect of Entrapped Air," Journal of Pharmaceutical Sciences 72(10):1189-1191 (1983).
Krowczynski, L., "Oral extended-release dosage forms: Principles of technology," Extended-Release Dosage Forms pp. 97-158 (1987).
Lachman, L., et al., "Sustained Release Dosage Forms," The theory and practice of industrial pharmacy pp. 430-456 (1986).
Lansoprazole Delayed-Release Capsules. (2010). In The United States Pharmacopeia (34th ed., pp. 3270-3271).
Leopold, C., "Coated dosage forms for colon-specific drug delivery," Pharm. Sci. & Tech. Today 2(5):197-204 (1999).
Leopold, C., "Eudragit® E as coating material for the pH-controlled drug release in the topical treatment of inflammatory bowel disease (IDB)," Journal of Drug Targeting 6(2):85-94 (1998).
Li, C., et al, "The use of hypromellose in oral drug delivery," J Pharm Pharmacol 57(5): 533 (2005).
Lichtenstein, G., "Mesalamine in the Treatment of Ulcerative Colitis: Novel Therapeutics Options," 5 Gastroenterology & Hepatology 5(1):65-73 (2009).
Lichtenstein, G., et al., "Review article: 5-aminosalicylate formulations for the treatment of ulcerative colitis—methods of comparing release rates and delivery of 5-aminosalicylate to the colonic mucosa," Alimentary Pharmacology & Therapeutics 28:663-673 (2008).
Lin, C., et al, "Hydrogels in controlled release formulations: Network design and mathematical modeling," Adv Drug Deilv Rev 58:1379-1408 (2006).
Meglumine. (2009). In Handbook of Pharmaceutical Excipients (6th ed., pp. 431-432).
Melia, C., et al., "Structure and behaviour of hydrophilic matrix sustained release dosage forms: 1. The origin and mechanism of formation of gas bubbles in the hydrated surface layer," Int'l J. of Pharmaceutics 100(1-3):263-269 (1993).
Melia, C., "Hydrophilic Matrix Sustained Release Systems Based on Polyscaccharide Carriers," Critical Reviews in Therapeutic Drug Carrier Systems 8(4):395-421 (1991).
Melia, C., et al., "Advantages and Disadvantages of Multiparticulate Dosage Systems," Multiparticulate oral dosage forms: technology and biopharmaceutics Melia, Washington & Wilson eds., pp. 136-142 (1994).
Mesalamine Extended Release Capsules. (1997). In The United States Pharmacopeia (23rd ed., pp. 3905-3906).
Mesalamine Extended-Release Capsules. (1994). In Pharmacopeial Forum 20(1):6757-6846.
Mesalamine Extended-Release Capsules. (2010). In The United States Pharmacopeia (34th Revision, pp. 3430).
Mesalamine Extended-Release Capsules. (2013). In US Pharmacopeia (36th Revision, pp. 4255-4256).
Miller, S. et al., "Effect of poloxamer 407 gel on the miotic activity of pilocarpine nitrate in rabbits" Int. J. Pharmaceutics 12:147-152 (1982).
Milojevic, Snezana et al., "Amylose as a coating for drug delivery to the colon: Preparation and in vitro evaluation using 5-aminosalicylic acid pellets," J. Controlled Release 38:75-84 (1996).
Morphine Sulfate (1996). In The Merck Index (12 ed. p. 6359).
Morphine. (1999). In Therapeutic Drugs 1:M225-232 (Dollery ed.).
Moustafine, R., et al., "Physicochemical characterization and drug release properties of Eudragit E PO/Eudragit® L 100-55 interpolyelectrolyte complexes," European Journal of Pharmaceutics and Biopharmaceutics 63:26-36 (2006).
Muller, A., et al., "Experience of 5-aminosalicylate nephrotoxicity in the United Kingdom" Alimentary Pharmacology and Therapeutics 21:1217-1224 (2005).
Müllers, I., et al., "Production of dosage forms for oral drug delivery by laminar extrusion of wet masses," Eur. J. Pharmaceutics Biopharmaceutics 84:626-632 (2013).
Muraoka, M., et al., "Evaluation of intestinal pressure-controlled colon delivery capsule containing caffeine as a model drug in human volunteers," J. of controlled Release 52:119-129 (1998).
Narasimhan, B. & Peppas, N. "Disentanglement and Reptation During Dissolution of Rubbery Polymers," J. Polym. Sci., Polym. Phys. 34:947-961 (1996).
Nielsen, O. "Kinetics of 5-aminosalicylic acid after jejunal installation in man," Br. J. Clin. Pharmac. 16:738-740 (1983).
Nokhodchi, A., et al, "Liquisolid Compacts: The Effect of Cosolvent and HPMC on Theophylline Release," Colloids & Surfaces B: Biointerfaces 79:262-269 (2010).
Nostrum W., et al, "Novel crosslinking methods to design hydrogels," Advanced Drug Delivery Reviews 54:13-36 (2002).
Nugent, S., et al "Intestinal luminal pH in inflammatory bowel disease: possible determinants and implications for therapy with aminosalicylates and other drugs," Gut 48:571-577 (2001).
Oliveira, L. et al., "Maintaining remission in ulcerative colitis—role of once daily extended release mesalamine," Drug Design, Development and Therapy 5:111-116 (2011).
Omidian, H., et al., "Swelling agents and devices in oral drug delivery," J Drug Del Sci Tech 18(2):83-93 (2008).
Pantoprazole. (1999). In Therapeutic Drugs 2:11-14 (Dollery ed.).
Patchan, M., et al., "Synthesis and properties of regenerated cellulose-based hydrogels with high strength and transparency for potential use as an ocular bandage," Mat. Sci. Eng. C 33:3069-3076 (2013).
Pentasa. (1998). In Physician's Desk Reference (52nd ed., pp. 1229).
Pentasa. (1999). In Physician's Desk Reference (53rd ed., pp. 2630).
Adkin, D., et al., "Colonic transit of different sized tablets in healthy subjects." J. Cont. Release 23:147-156 (1993).
Alderman D., "A review of cellulose ethers in hydrophilic matrices for oral controlled-release dosage form." Int J Pharm Tech Prod Manuf 5:1-9 (1984).
Alvarez, L. et al, "Effect of Microcrystalline Cellulose Grade and Process Variables on Pellets Prepared by Extrusion-Spheronization." Drug Develop Ind Pharm 28:451-456 (2002).
Asacol. (1996). In Physician's Desk Reference (50th ed., pp. 1979-1981).
Asacol. (1998). In Physician's Desk Reference (52d ed., pp. 2312-2313).
Asacol. (1999). In Physician's Desk Reference (53d ed., pp. 2538-2539).
Ashford, M., et al., "Targeting Drugs to the Colon: Delivery Systems for Oral Administration." J. Drug Targeting 2:241-258 (1994).
Ashford, M., et al., "An In Vivo Investigation into the Suitability of pH Dependent Polymers for Colonic Targeting." Int'l J. Pharm. 95:193-199 (1993).
Azulfidine. (1997). In Physician's Desk Reference (51st ed., pp. 2059-2060).
Azulfidine. (1998). In Physician's Desk Reference (52d ed., pp. 2239-2241).
Azulfidine. (1999). In Physician's Desk Reference (53d ed., p. 2454).
Banerjee, S., et al., "Compressive textural attributes, opacity and syneresis of gels prepared from gellan, agar and their mixtures." Journal of Food Engineering 102:287-292 (2011).

(56) References Cited

OTHER PUBLICATIONS

Barrow, L. et al., "Pathological influences on colonic motility: implications for drug delivery." Adv. Drug Delivery Reviews 7:201-218 (1991).
Bettini, R., et al, "Polymer relaxation in swellable matrices contributes to drug release." Proceed Int Symp Control Rel Bioact Mater 25:36-37 (1998).
Bettini, R., et al, "Swelling and drug-release in hydrogel matrices-polymer viscosity and matrix porosity effects." Eur J Pharm Sci 2: 213-219 (1994).
Brzezinski, A., et al., "Use of old and new oral 5-aminosalicylic acid formulations in inflammatory bowel disease." Cleveland Clinical Journal of Medicine 62:317-323 (1995).
Budesonide. (1999). In Therapeutic Drugs 1: B88-92 (Dollery ed.).
Campregher, C., "Aminosalicylates. Best Practice & Research Clinical Gastroenterology." 25: 535-546 (2011).
Carothers, W., "Polymers and polyfunctionality" Trans Faraday Soc 32: 39-49 (1936).
Chambliss, W., "Enteric Coatings" In Encyclopedia of Pharmaceutical Technology 5 (1992).
Chang, R., et al., "Sustained Drug Release in Tablets and Particles Through Coating." In Pharmaceutical Dosage Forms: Tablets 199-302 (Lieberman et al., eds. 2nd Ed. 1990).
Chatlapalli R., et al, "Physical characterization of HPMC and HEC and investigation of their use as pelletization aids." Intl Journal of Pharmaceutics 161: 179-93 (1998).
Christensen, L., et al., "Topical and systemic availability of 5-aminosalicylate: comparisons of three controlled release preparations in man." Aliment. Pharmacol. Therap. 4: 523-533 (1990).
Coffey, D., et al, "Cellulose and cellulose derivatives." In Food polysaccharides and their applications (Marcel Dekker, NY, pp. 125-153) (1995).
Cohen, R., "Review article: evolutionary advances in the delivery of aminosalicylates for the treatment of ulcerative colitis." Alimentary Pharmacology & Therapeutics 24:465-474 (2006).
Cohen, R., "Is There a Role for Rectal Therapy in the Treatment of Inflammatory Bowel Disease?" Gastroenterology & Hepatology 6:309-316 (2010).
Colombo, P., et al., "Drug release modulation by physical restrictions of matrix swelling." Int J Pharm 63:43-48 (1990).
Colombo, P., et al., "Swelling-controlled release in hydrogel matrices for oral route." Adv Drug Deliv Rev 11: 37-57 (1993).
Colombo, P., et al., "Sweallable matrices for controlled drug delivery: gel-layer behavior, mechanisms and optimal performance." PSTT 3:198-204 (2000).
Columbo, P., et al., Chapter 9 in Handbook of Pharmaceutical Controlled Release Technology. (D. Wise ed., p. 183-209) (2000).
Corrigan, G., et al., "Review article: interstitial nephritis associated with the use of mesalazine in inflammatory bowel disease." Alimentary Pharmacology & Therapeutics 14:1-6 (2000).
Costa, P., et al., "Modeling and Comparison of Dissolution Profiles." Eur J Pharm Sci 13:123-133 (2001).
Coupe, A., et al., "Variation in Gastrointestinal Transit of Pharmaceutical Dosage Forms in Healthy Subjects," Pharmaceutical Research 8:360-364 (1991).
D.I. No. 118—Order Construing the Terms of U.S. Patent Nos. 6,551,620; 7,547,451; 8,337,886; and 8,496,965 (Dec. 17, 2013).
Daniel-da-Silva, A., et al, "Impact of Magnetic Nanofillers in the Swelling and Release Properties of K-Carrageenan Hydrogel Nanocomposites," Carbohyd Polym 87: 328-335 (2012).
Daumesnil, R., "Marketing Considerations for Multiparticulate Drug Delivery Systems." in Multiparticlate Oral Drug Delivery 457-475 (Ghebre-Sellassie ed., 1994).
Davis, S., et al., "Gastrointestinal Transit of a Multiparticulate Tablet Formulation in Patients with Active Ulcerative Colitis." Int'l J. Pharmaceutics 68:199-204 (1991).
Davis, S. et al. "Transit of pharmaceutical dosage forms through the small intestine." Gut 27:886-892 (1986).
De Souza, Dayse Fernanda, et al., "Development of enteric coated sustained release minitablets containing mesalamine." Brazilian J. of Pharmaceutical Sciences 529-536 (2013).
Deasy, Patrick B., Chapter 2: Core and Coating Properties 21-60 & Chapter 7: Air Suspension Coating 161-179 In Microencapsulation and Related Drug Processes. (1984).
Deo, S.C., et al., "Development of mesalazine pellets coated with methacrylic-derived polymer." Brazilian Journal of Pharmaceutical Sciences 47:103-109 (2011).
Dew, M.J., et al. "5-aminosalicylic acid for the treatment of inflammatory bowel disease." Gastroenterology 87: 480-481 (1984).
Dignass, A.U., et al., "Mesalamine Once Daily is More Effective Than Twice Daily in Patients With Quiescent Ulcerative Colitis." Clinical Gastroenterology and Hepatology 7:762-769 (2009).
Dipentum. (1998). In Physician's Desk Reference (52d ed., pp. 2264-2265).
Dipentum. (1999). In Physician's Desk Reference (53d ed., p. 2480).
Doelker, E., "Cellulose Derivatives.", Adv Polym Sci 107:199-265 (1993).
Dombal, F., "Ulcerative colitis: definition, historical background, aetiology, diagnosis, natural history and local complications." Postgrad. Med. J, 44:684-692 (1968).
Donald, I., et al., "The value of 5-aminosalicylic acid in inflammatory bowel disease for patients intolerant or allergic to sulphasalazine." Postgraduate Medical Journal 61:1047-1048 (1985).
Dow Brochure: Formulating for Controlled Release with METHOCEL Premium cellulose ethers (1995).
Dow Brochure: Using Dow Excipients for Controlled Release of Drugs in Hydrophilic Matrix Systems (2006).
De Brant, et al., "Influence of Hydrophilic Additives on 5-Aminosalicylic Acid Release Rate from Matrix Pellets", 5th International Conference on Pharmaceutical Technology, Laboratory for Pharmaceutical Technology, State University of Gent, Belgium, 1989, vol. 5, pp. 222-230.

PELLET FORMULATION FOR THE TREATMENT OF THE INTESTINAL TRACT

RELATED APPLICATIONS

This application is a Continuation of U.S. application Ser. No. 13/586,585, Granted as U.S. Pat. No. 8,496,965, which is a Continuation of U.S. application Ser. No. 12/236,157 filed on Sep. 23, 2008, Granted as U.S. Pat. No. 8,337,886, which is a Continuation of U.S. application Ser. No. 10/360,410 filed on Feb. 7, 2003, Granted as U.S. Pat. No. 7,547,451, which is a Divisional of U.S. application Ser. No. 09/906,494 filed on Jul. 16, 2001, Granted as U.S. Pat. No. 6,551,620, which is a Continuation of U.S. application Ser. No. 09/194,213 filed on Aug. 30, 1999, Granted as U.S. Pat. No. 6,277,412, which is a filing under 35 U.S.C. 371 of Application No. PCT/EP98/02319 filed on Apr. 20, 1998, which claims priority from German Application No. 197 32 903.9, filed Jul. 30, 1997. The entire contents of the aforementioned applications are hereby incorporated by reference.

FIELD OF THE INVENTION

The present invention relates to a pellet formulation for the treatment of the intestinal tract, which comprises, as a pharmaceutical active compound, aminosalicylic acid or a pharmaceutically tolerable salt or derivatives thereof.

BACKGROUND OF THE INVENTION

The active compound aminosalicylic acid (in particular 5-ASA) or its derivatives have been used successfully for a relatively long time for the treatment of intestinal disorders, such as, for example, ulcerative colitis and Crohn's disease (DE 31 51 196 A1).

The use of 5-ASA and its derivatives as a chemotherapeutic agent in colonic cancer is likewise known, polyps in the colon and rectum being associated with an increased risk of carcinoma (WO 95/18622).

A coloscopic polypectomy in patients with polyps in the colon and/or rectum results in a considerable reduction in risk of the formation of colonic carcinomas and is recommended as a therapy, in particular in the case of colorectal polyps. The recurrence rate after polypectomy, however, is high and amounts to about 6-30% per year. Aminosalicylic acid is suitable for the longer-term treatment of such patients and lowers the recurrence rate of colorectal polyps.

The action of aminosalicylic acid in the treatment of intestinal disorders, or in the prevention of their recurrence or in the prevention of secondary disorders arising therefrom and possible accompanying disorders takes place by means of the contact of the active compound directly at the site of the disorder in the intestine, the action of the aminosalicylic acid, or a derivative thereof, being directly related to its local concentration in the intestinal area to be treated.

Since inflammatory processes often affect relatively large sections of the intestinal tract, the pharmaceutical form should spread reproducibly over wide areas of the intestine and release the active compound only at the site of inflammation.

A problem in the treatment with aminosalicylic acid is that the active compound is very easily absorbed and can be excreted via the kidney before its action can occur.

In the prior art, tablets and pellets are known which are coated with an enteric coating in order to thus prevent a premature release of the active compounds.

FR-A2 692 484 discloses a tablet for the controlled release of 4-ASA in a hydrophilic matrix which consists of swellable polymers forming a gel barrier, and having an enteric coating. After dissolution of the coating, the matrix swells and forms a gel barrier through which the active compound diffuses out. After an approximately two-hour lag phase, the composition disclosed in FR-A 2 692 484 releases the active compound approximately linearly in the intestine over a period of time of a further 14 h.

EP 0 453 001 A1 discloses a pharmaceutical composition in which the active compound is covered with at least two membranes, of which one is soluble at a pH of ≥5.5 and the other is insoluble at this pH but is permeable to the intestinal fluids.

EP 0 148 811 A1 discloses a pharmaceutical composition which consists of a core which contains the active compound. The core is surrounded by two layers, of which the inner layer is a diffusion membrane and the second layer is an anionic polymer and/or a fatty acid having a $pK_a$ of 4.5 to 7.

EP 0 629 398 A1 discloses pharmaceutical compositions in which the active compound-containing core is surrounded by an enteric phase. According to Example 2, the core can contain small amounts of hydroxypropyl-cellulose. The active compound should be released rapidly after dissolution of the enteric phase.

EP 0 485 840 A2 discloses an oral pharmaceutical form which contains a shell material surrounding the active compound consisting of a polysaccharide and a film-forming polymer material.

A disadvantage in the case of the pharmaceutical formulations known in the prior art is that the active compound is also absorbed into the blood circulation. This amount of active compound is thus lacking in the intestine, so that the effective dose of the medicament is reduced by the part of the active compound which is found in the blood.

Moreover, patients who suffer from intestinal disorders frequently have to be further treated over relatively long periods with the active compound, or derivatives thereof, after the acute disorder has died down in order to prevent the disorder flaring up again or secondary disorders resulting from the original disorder. In the case of such a long-term treatment, however, it has proven to be a problem that a certain nephrotoxicity of systemically available 5-ASA, i.e. 5-ASA found in the bloodstream, or derivatives thereof cannot be excluded (M. Barry, Prescribers Journal, 1992, 32, 205).

It is thus an object of the present invention make available an orally administrable pharmaceutical formulation which does not have these disadvantages. According to the invention, formulations are therefore made available which have a controlled release profile which results in a high local active compound concentration at the site of action and simultaneously guarantees a blood level of the active compound which is as low as possible.

In the context of the present invention, it has now been found that pellet formulations are particularly suitable for this purpose, since unlike a tablet they spread the pharmaceutical form reproducibly over wide areas of the intestine and are thus particularly suitable for treatment of inflammatory processes, which often affect relatively large sections of the intestinal tract. In order to achieve the necessary local active compound concentration, the active compound must in this case be released at the site of inflammation within a relatively short time (up to a few hours) without, however, it being released virtually immediately, in order that its action does not wear off too rapidly.

The use of a swellable, gel-forming matrix such as described in FR-A 2 692 484 is not suitable for pellets having a diameter of 3 mm, since on account of the small diameter the polymer is very rapidly penetrated by the water, eroded as a result, and the active compound would thus be released virtually immediately (about 30 min).

In the context of the present invention, however, it has surprisingly been found that, if the active compound is present in the pellet core in a non gel-forming polymer matrix which is essentially insoluble and permeable to intestinal fluids and the active compound, a markedly reduced release of the active compound into the blood, with simultaneously increased local concentration of the active compound at the site of the disorder in the intestine, is guaranteed in comparison with aminosalicylic acid formulations already known in the prior art.

The present invention thus relates to an orally administrable pharmaceutical pellet formulation having a controlled release profile for the treatment of the intestinal tract, which comprises a core and an enteric coating, and, if appropriate, further pharmaceutically tolerable additives, the core including as a pharmaceutically active compound aminosalicylic acid or a pharmaceutically tolerable salt or derivative thereof, wherein the active compound is present in the core in a non gel-forming polymer matrix which is essentially insoluble in the intestinal tract and permeable to intestinal fluids and the active compound, the matrix-forming polymer making up at least 1% by weight of the total weight of the core.

The invention furthermore relates to a process for the production of the pellets described above and their use for the production of a medicament for the treatment of intestinal disorders, such as inflammatory intestinal disorders, preferably in the active phase and/or in the remission phase, for the prevention of these disorders, for the prevention of the recurrence of these disorders or secondary disorders resulting therefrom, and of possible accompanying disorders and also for the treatment of intestinal cancer. The medicament is particularly suitable for the treatment of inflammatory intestinal disorders such as Crohn's disease and ulcerative colitis, and for the prevention, treatment and/or prevention of the reformation of polyps in the gastrointestinal tract. Moreover, the medicament is suitable for the prevention of colorectal carcinomas in patients with adenomas and/or polypous growth, in particular with polypous growth in the intestine. The medicament is moreover used for lowering the recurrence rate of colorectal polyps.

Preferred active compounds are 5-aminosalicylic acid (also called mesalazine), 4-aminosalicylic acid and, serving as a prodrug for 5-ASA, 2-hydroxy-5-phenylazobenzoic acid derivatives such as sulfasalazine (5-[4-(2-pyridylsulfamoyl)phenylazo]salicylic acid) and balsalazide (the sodium salt of the azo derivative of 4-aminobenzoyl-β-alanine and 5-aminosalicylic acid). 5-ASA is particularly preferred.

In addition to the active compound, the pellet core comprises 1% by weight, based on the total weight of the core, of a matrix-forming, non gel-forming polymer which is essentially insoluble in the intestinal tract and permeable to intestinal fluids and the active compound. Suitable matrix-forming polymers are, for example, those polymers which are known in the prior art as coating lacquers for delayed-release pharmaceuticals, such as, for example, (meth)acrylic ester copolymers.

Among the polymers which are essentially insoluble in the intestinal tract and permeable to intestinal fluids and the active compound, those are preferred which are insoluble or particularly preferably water-insoluble in the intestinal tract.

Methyl acrylate copolymers and ammoniomethacrylate copolymers of the type such as can be obtained under the tradename Eudragit® RS/RL/NE are particularly preferred.

As functional groups, these polymers have ester groups (Eudragit® NE) or ammonium groups (Eudragit® RL/RS). Poly(ethyl acrylate, methyl methacrylate) and poly(ethyl acrylate, methyl methacrylate, trimethylammonioethyl methacrylate chloride) are preferred. These polymers are obtainable, for example, as poly(ethyl acrylate, methyl methacrylate) 2:1 in 40% strength aqueous dispersion as Eudragit® NE 40 D and as poly(ethyl acrylate, methyl methacrylate, trimethylammonioethyl methacrylate chloride) 1:2:0.1 in 12.5% strength isopropanolic solution as Eudragit® RS 12.5 and in the composition 1:2:0.2 as Eudragit® RL 12.5. The most preferred is Eudragit® NE 40 D.

The polymer must be present in an amount which is sufficient to form a matrix for the active compound and which guarantees a delayed release of the active compound. For this purpose, an amount of at least 1% by weight, preferably at least 4% by weight, based on the total weight of the core, has proven suitable. Larger amounts of, for example, approximately 21% by weight can also be employed. 4% by weight to 10% by weight is preferably employed.

The active compound is preferably homogeneously dispersed in the matrix described above and is released with a delay after dissolving the enteric coating. The matrix with the active compound homogeneously dispersed therein advantageously extends through the entire core.

The enteric coating should only dissolve after the formulation has left the stomach. Necessary coatings for this purpose are disclosed in the prior art (e.g. EP 0 453 001 A1).

Preferred enteric coatings according to the invention comprise a methacrylic acid copolymer or methylhydroxypropylcellulose phthalate. Poly(methacrylic acid, methyl methacrylates), which are obtainable under the tradenames Eudragit® L or S and have free carboxyl groups as functional groups, are preferred. These polymers are insoluble in the gastric juice, but dissolve in digestive juices above pH 5.5-7 depending on the number of functional carboxyl groups. Poly(methacrylic acid, methyl methacrylate) 1:1 (Eudragit® L 100; methacrylic acid copolymer, USP/NF type A) and poly(methacrylic acid, methyl methacrylate) 1:2 (Eudragit® S; methacrylic acid copolymer, USP/NF type B) are particularly preferred. Eudragit® L 100 is the most preferred. Mixtures of the coating materials mentioned, in particular of Eudragit® L and Eudragit® S, can also be used.

The pellet formulation can comprise one or more coatings, however pellet formulations in which the pellet only comprises one coating are preferred.

Both the core and the coating of the pellet formulation according to the invention can include one or more of the abovementioned matrix or coating materials.

The pellet formulations according to the invention can additionally contain further pharmaceutically tolerable additives both in the core and in the coating. Examples of pharmaceutically tolerable additives include polyvinylpyrrolidone, microcrystalline cellulose, silica, magnesium stearate, lactose, cornstarch, triethyl citrate, talc, titanium dioxide and polyethylene glycol.

A particularly preferred pellet formulation according to the present invention comprises 5-ASA as an active compound in the core in a poly(ethyl acrylate, methyl methacrylate) 2:1 matrix, the polymer containing ester groups as functional groups, and an enteric coating which contains poly(methacrylic acid, methyl methacrylate) 1:1 or 1:2 with free carboxyl groups as functional groups, and, if appropriate, further pharmaceutically tolerable additives.

Moreover, a mixture of Eudragit® S and Eudragit® L, preferably approximately 1:1, is advantageously employed in a coating for the pellet formulations according to the invention.

The pellet formulation according to the invention is distinguished by a controlled release profile. Preferably, the release of active compound in 0.1 M HCl after 2 h is <10%, in particular <5%, and in artificial gastric juice at pH 6.8 after 0.5 h 10-30%, in particular 10-20%, after 2 h 40-60%, in particular 40-50%, and after 6 h at least 80%, in particular at least 85%.

The pellet formulations according to the invention can be prepared according to conventional processes known to the person skilled in the art. For example, the matrix material is first mixed with the active compound and, if appropriate, the further pharmaceutically tolerable additives and shaped to give pellets. The coating is then applied, e.g. sprayed on, in the form of a lacquer suspension in a suitable suspending agent such as ethanol and/or water. The pellets can in this case have a size of 0.1-3 mm, preferably 0.5-1 mm, and are combined in unit dose forms such as tablets or capsules for the production of a medicament. The present invention therefore also relates to pharmaceutical formulations which comprise the pellets according to the invention, in particular gelatin capsules which contain the pellets according to the invention.

On oral administration, the pellet formulations thus obtained result, in comparison with other preparations with the same active compound, in lower active compound concentrations in the blood with a simultaneously higher concentration of the active compounds in the intestine, as a result of which the side effect potential caused by the systemically available active compound or its metabolites, is markedly reduced.

The pellet formulation according to the invention is thus particularly suitable for the treatment of intestinal conditions in which a relatively long-term administration of the active compound is indicated, such as inflammatory intestinal disorders in their active phase and their remission phase, in the prevention of adenomas and/or polyp formation, in the prevention of the recurrence of adenomas and/or polyps and in the prevention of secondary disorders resulting therefrom and possible accompanying disorders.

Figure 2:
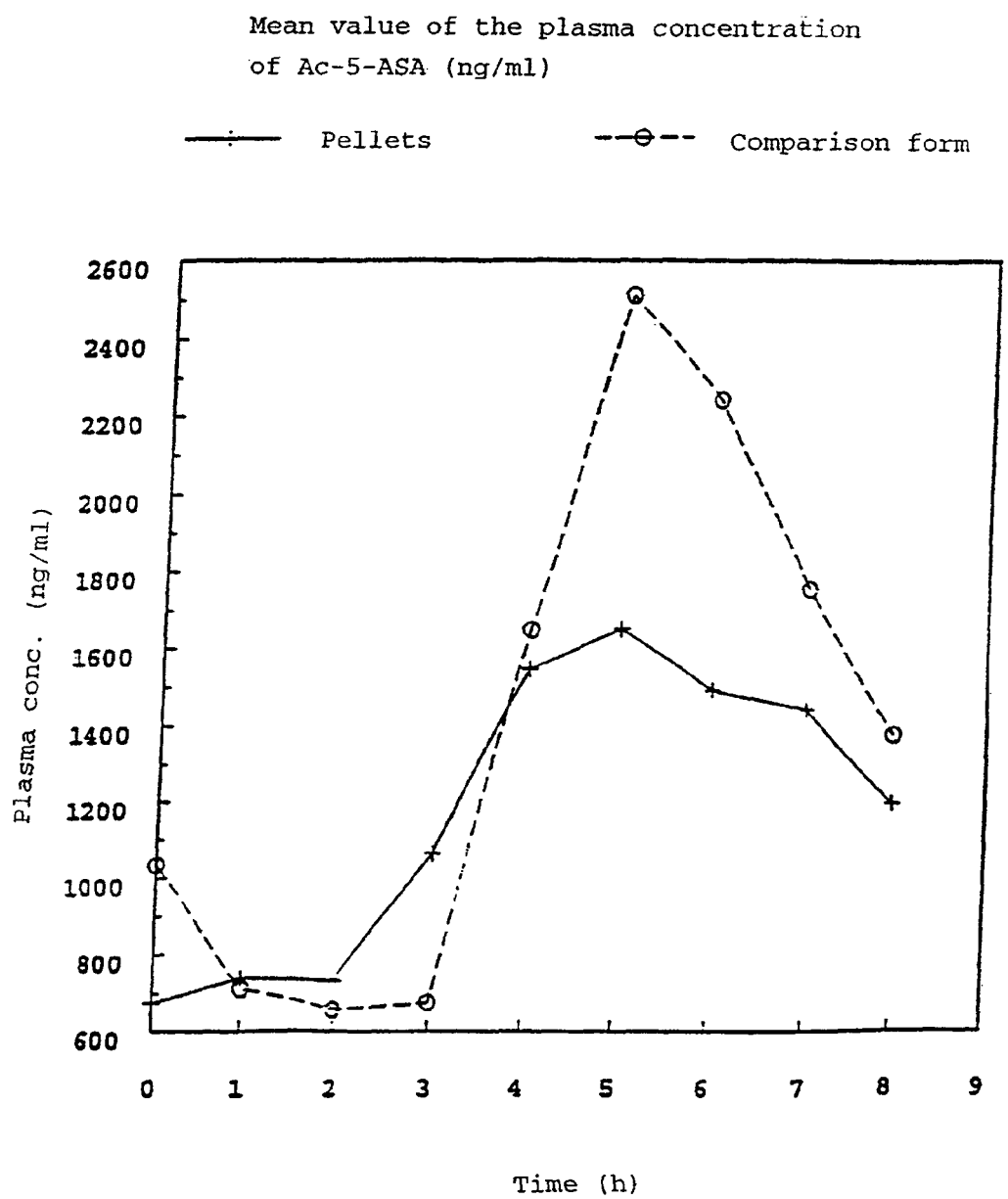

FIGS. 1 and 2 show graphs of the plasma concentrations of 5-ASA (FIG. 1) and Ac-5-ASA (FIG. 2) against time.

The following examples serve to illustrate the invention.

Example 1 describes two different pellet cores (Example 1.1-1.2) and four different pellet coatings (Example 1.a-1.d). The different cores can be combined in any desired manner with the different coatings, the pellet core from Example 1.1 together with the coating from Example 1.a being a particularly preferred example.

EXAMPLE 1

Examples of Pellet Cores 1.1

| I | Mesalazine | 5000 g |
|---|---|---|
| II | Cellulose, microcrystalline | 1500 g |
| III | Hydroxypropylmethylcellulose | 200 g |
| IV | Silica | 25 g |
| V | Poly(ethyl acrylate, methyl methacrylate) 2:1 as a 40% strength aqueous dispersion, tradename Eudragit ® NE 40 D | 750 g |
| VI | Magnesium stearate | 250 g |

I-IV are mixed, moistened with V and intensively kneaded. VI is finally scattered in. The moist mass is pressed through an extruder with a die bore of 1 mm. The extruded pellets are cut into pieces about 1 mm long and rounded in a spheronizer. The pellets are dried at 60° C.

1.2

| I | Mesalazine | 5000 g |
|---|---|---|
| II | Cellulose, microcrystalline | 1500 g |
| III | Hydroxypropylmethylcellulose | 200 g |
| IV | Silica | 25 g |
| V | Poly(ethyl acrylate, methyl methacrylate, trimethylammonioethyl methacrylate chloride) 1:2:0.1; as a 12.5% strength isopropanolic solution; tradename Eudragit ® RS 12.5 | 2500 g |
| VI | Magnesium stearate | 250 g |

I-IV are mixed, moistened with V and intensively kneaded. VI is finally scattered in. The moist mass is pressed through an extruder with a die bore of 1 mm. The extruded pellets are cut into pieces about 1 mm long and rounded in a spheronizer. The pellets are dried at 60° C.

Examples of Pellet Coatings

Formulations for 5000 g pellets, corresponding to Examples 1.1-1.2

1.a

| I | Poly(methacrylic acid, methyl methacrylate) 1:1; tradename Eudragit ® L 100; (methacrylic acid copolymer, USP/NF type A) | 750 g |
|---|---|---|
| II | Triethyl citrate | 75 g |
| III | Talc | 200 g |
| IV | Titanium dioxide | 125 g |
| V | Magnesium stearate | 50 g |

I is dissolved in 7000 g of an ethanol/water mixture (8:2). II-V are suspended in the solution; the lacquer suspension is sprayed on at a feed air temperature of 40° C. in a suitable apparatus.

1.b

| I | Poly(methacrylic acid, methyl methacrylate) 1:2; tradename Eudragit ® S; (methacrylic acid copolymer, USP/NF type B) | 350 g |
|---|---|---|
| II | Triethyl citrate | 35 g |
| III | Talc | 100 g |
| IV | Titanium dioxide | 125 g |
| V | Magnesium stearate | 50 g |

I is dissolved in 3500 g of an ethanol/water mixture (8:2). II-V are suspended in the solution; the lacquer suspension is sprayed on at a feed air temperature of 40° C. in a suitable apparatus.

1.c

| I | Poly(methacrylic acid, methyl methacrylate) 1:2; tradename Eudragit ® S; (methacrylic acid copolymer, USP/NF type B); poly(methacrylic acid, methyl methacrylate) 1:1; tradename Eudragit ® L 100; (methacrylic | 420 g |
|---|---|---|

-continued

|     |                                                                       |       |
| --- | --------------------------------------------------------------------- | ----- |
|     | acid copolymer, USP/NF type A) (mixed in the ratio 1.1:1)             |       |
| II  | Triethyl citrate                                                      | 75 g  |
| III | Talc                                                                  | 200 g |
| IV  | Titanium dioxide                                                      | 125 g |
| V   | Magnesium stearate                                                    | 50 g  |

I is dissolved in 5000 g of an ethanol/water mixture (8:2). II-V are suspended in the solution; the lacquer suspension is sprayed on at a feed air temperature of 40° C. in a suitable apparatus.

1.d

|     |                                |       |
| --- | ------------------------------ | ----- |
| I   | Methylhydroxypropylcellulose phthalate | 410 g |
| II  | Ethylcellulose                 | 44 g  |
| III | Polyethylene glycol 6000       | 40 g  |
| IV  | Talc                           | 200 g |
| V   | Titanium dioxide               | 125 g |
| VI  | Magnesium stearate             | 50 g  |

I and II are dissolved in 5000 g of an ethanol/water mixture (9:1). III-VI are suspended in the solution; the lacquer suspension is sprayed on at a feed air temperature of 40° C. in a suitable apparatus.

EXAMPLE 2

To determine the release of the active compound from the pellets according to the invention, the "basket" method was used. The stirrer speed was 100 rpm and the temperature was kept constant at 37° C. 0.1 M HCl according to USP was used as artificial gastric juice and USP phosphate buffer (pH 6.8) as artificial intestinal juice.

Table 1 indicates the active compound release of the pellet formulation according to the invention having a core according to Example 1.1 and a coating according to Example 1.a under the abovementioned conditions.

TABLE 1

| pH  | Time [min] | Release [%] |
| --- | ---------- | ----------- |
| 1.2 | 120        | 1.6         |
| 6.8 | 30         | 12.2        |
|     | 60         | 24.9        |
|     | 90         | 36.0        |
|     | 120        | 45.2        |
|     | 150        | 53.0        |
|     | 180        | 59.7        |
|     | 240        | 70.6        |
|     | 300        | 78.8        |
|     | 360        | 85.4        |

EXAMPLE 3

In order to obtain results about the active compound absorption into the blood after administration of the pellet formulation according to the invention, the plasma concentrations of 5-ASA and acetyl-5-ASA (Ac-5-ASA), its degradation product, were investigated in a time-dependent manner. In a cross-over arrangement, 24 healthy subjects received 500 mg of 5-ASA in two different pharmaceutical formulations (pellets according to the invention having a core according to Example 1.1 and coating according to Example 1.a and commercially available Salofalk® tablets (mesalazine in the form of enteric tablets) as a comparison preparation) over a period of 4 days (3×500 mg of 5-ASA daily). To determine the plasma concentration of 5-ASA and acetyl-5-ASA, venous blood samples were taken from the subjects.

Tab. 2 shows the plasma concentration of 5-ASA and Ac-5-ASA averaged from 24 patients under steady-state conditions.

TABLE 2

Plasma concentration of 5-ASA and Ac-5-ASA in 24 subjects [ng/ml] (mean value)

| Time after administration | Pellets | | Comparison preparation | |
| --- | --- | --- | --- | --- |
| [h] | [5-ASA] | [Ac-5-ASA] | [5-ASA] | [Ac-5-ASA] |
| 0 | 63.49 | 676.35 | 198.42 | 1033.89 |
| 1 | 71.50 | 739.46 | 96.66 | 711.70 |
| 2 | 102.97 | 731.34 | 82.86 | 657.16 |
| 3 | 382.02 | 1063.59 | 156.55 | 675.83 |
| 4 | 686.03 | 1549.00 | 1293.30 | 1651.01 |
| 5 | 527.39 | 1653.73 | 1564.33 | 2511.99 |
| 6 | 456.70 | 1493.00 | 924.75 | 2243.11 |
| 7 | 384.25 | 1442.96 | 492.91 | 1755.05 |
| 8 | 257.16 | 1196.51 | 275.11 | 1377.46 |

It is evident from Table 2 and from FIGS. 1 and 2 that markedly lower plasma levels can be achieved both from 5-ASA and from its metabolite Ac-5-ASA if 5-ASA is administered to the subjects in the form of the pellet formulation according to the invention. This result is confirmed by the average $C_{max}$ values (average of the $C_{max}$ values calculated from the data of the individual subjects). In the case of the comparison formulation, the average $C_{max}$ value was 2001 ng/ml for 5-ASA and 2617 ng/ml for Ac-5-ASA while in the case of the pellet formulation according to the invention the average $C_{max}$ value was 755 ng/ml for 5-ASA and 1810 ng/ml for Ac-5-ASA. The average $C_{max}$ value of the pellet formulation is thus only 37.7% of the average $C_{max}$ value of the comparison formulation for 5-ASA and only 69% for Ac-5-ASA.

EXAMPLE 4

In order to confirm an increased local release of the 5-ASA in the intestine, feces samples of 4 subjects who had received 1500 mg of 5-ASA were investigated for 5-ASA and Ac-5-ASA in a further investigation. To this end, the feces of the subjects were collected for 71 hours and investigated for free 5-ASA and Ac-5-ASA which were not bound in the pellet or in the comparison formulation (Tab. 3). The pellets according to the invention employed were those having a core according to Example 1.1 and a coating according to Example 1.a; the comparison preparation used was commercially available Salofalk® tablets (mesalazine in the form of enteric tablets).

TABLE 3

Cumulative fecal excretion of 5-ASA and 5-Ac-ASA of 4 subjects [mg] (mean value)

| Pellets | | Comparison preparation | |
| --- | --- | --- | --- |
| [5-ASA] | [Ac-5-ASA] | [5-ASA] | [Ac-5-ASA] |
| 287.5 | 367.9 | 222.9 | 275.7 |

It is evident from the table that both the amount of the 5-ASA released in the intestine by the pellet formulation according to the invention, at 287.5 mg, and the amount of free Ac-5-ASA, at 367.9 mg, is higher by 29% or 44% respectively than in the comparison formulation. Since Ac-5-ASA can only be formed in the intestine by the interaction with the intestinal mucous membrane, the increased amount of Ac-5-ASA in the pellet formulation shows that markedly more active compound comes into contact with the intestinal mucous membrane and can thus display its curative action than in the comparison formulation.

These investigations confirm that the concentration of the active compound 5-ASA or its degradation product Ac-5-ASA in the blood can be significantly lowered by the pellet formulation according to the invention in comparison with commercially available 5-ASA preparations and thus the danger of possible side effects (nephrotoxicity etc.) is also lower. As a result of the reduced absorption of the active compound into the blood, markedly higher amounts of the active compound are available in the intestine. These also come into contact with the intestinal mucous membrane and can display their action there, as the amounts of Ac-5-ASA, which are higher in comparison with the comparison formulation and which are formed in the intestine by the direct contact of 5-ASA with the intestinal mucous membrane, confirm. Unlike the systemically available 5-ASA and Ac-5-ASA, the 5-ASA and Ac-5-ASA present in the intestine cannot have a nephrotoxic action, since it is not excreted via the kidney, but with the feces.

Thus the pellet formulation according to the invention is preferably suitable for intestinal conditions in which a relatively long-term administration of the active compound is indicated, such as inflammatory intestinal disorders in their active phase and in their remission phase, in the prevention of polyp formation, in the prevention of the recurrence of polyps and in the prevention of secondary disorders resulting therefrom and possible accompanying disorders.

The invention claimed is:

1. An orally administrable pharmaceutical pellet formulation having a controlled release profile for the treatment of the intestinal tract, which comprises a core and an enteric coating, the core including aminosalicylic acid or a pharmaceutically acceptable salt thereof, wherein the aminosalicylic acid or pharmaceutically acceptable salt thereof is present in the core and homogenously dispersed in a non gel-forming polymer matrix comprising poly (ethylacrylate, methyl methacrylate) (2:1), wherein the polymer matrix is essentially insoluble in the intestinal tract and permeable to intestinal fluids and the aminosalicylic acid.

2. The pellet formulation of claim 1, wherein the poly (ethylacrylate, methyl methacrylate) (2:1) is present as a 40% strength aqueous dispersion.

3. The pellet formulation of claim 1, wherein the enteric coating comprises poly(methacrylic acid, methyl methacrylate) 1:1 or 1:2 with free carboxyl groups as functional groups.

4. The pellet formulation of claim 3, wherein the enteric coating comprises poly(methacylic acid-co-methyl methacrylate) 1:2 and poly(methacylic acid-co-methyl methacrylate) 1:1.

5. The pellet formulation of claim 1, wherein the matrix-forming polymer makes up at least 1% and up to approximately 21% by weight of the total weight of the core.

6. The pellet formulation of claim 1, wherein the pellet formulation is a capsule.

7. The pellet formulation of claim 1, wherein the pellets formulation is a tablet.

8. The pellet formulation of claim 1, wherein the pellets have a size of 0.1 to 3 mm.

9. The pellet formulation of claim 1, wherein the polymer matrix is water-insoluble in the intestinal tract.

10. An orally administrable pharmaceutical pellet formulation having a controlled release profile for the treatment of the intestinal tract, which comprises a core and an enteric coating, the core including aminosalicylic acid or a pharmaceutically acceptable salt thereof, wherein the aminosalicylic acid or pharmaceutically acceptable salt thereof is present in the core and homogenously dispersed in a polymer matrix comprising poly (ethylacrylate, methyl methacrylate) (2:1), wherein the polymer matrix is essentially insoluble in the intestinal tract and permeable to intestinal fluids and the aminosalicylic acid.

11. The pellet formulation of claim 10, wherein the poly (ethylacrylate, methyl methacrylate) (2:1) is present as a 40% strength aqueous dispersion.

12. The pellet formulation of claim 10, wherein the enteric coating comprises poly(methacrylic acid, methyl methacrylate) 1:1 or 1:2 with free carboxyl groups as functional groups.

13. The pellet formulation of claim 12, wherein the enteric coating comprises poly(methacylic acid-co-methyl methacrylate) 1:2 and poly(methacylic acid-co-methyl methacrylate) 1:1.

14. The pellet formulation of claim 10, wherein the matrix-forming polymer makes up at least 1% and up to approximately 21% by weight of the total weight of the core.

15. The pellet formulation of claim 10, wherein the polymer matrix comprises a non gel-forming polymer.

16. The pellet formulation of claim 10, wherein the matrix forming polymer makes up 10% by weight of the total weight of the core.

17. The pellet formulation of claim 10, wherein the polymer matrix is water-insoluble in the intestinal tract.

18. An orally administrable pharmaceutical pellet formulation having a controlled release profile for the treatment of the intestinal tract, which comprises a core and an enteric coating, the core including aminosalicylic acid or a pharmaceutically acceptable salt thereof, wherein the aminosalicylic acid or pharmaceutically acceptable salt thereof is present in the core and homogenously dispersed in a polymer matrix comprising poly (ethylacrylate, methyl methacrylate) (2:1), wherein the polymer matrix essentially insoluble in the intestinal tract and permeable to intestinal fluids and the aminosalicylic acid, and wherein the pellets have a size of 0.1 to 3 mm.

19. The pellet formulation of claim 18, wherein the poly (ethylacrylate, methyl methacrylate) (2:1) is present as a 40% strength aqueous dispersion.

20. The pellet formulation of claim 18, wherein the enteric coating comprises poly(methacrylic acid, methyl methacrylate) 1:1 or 1:2 with free carboxyl groups as functional groups.

21. The pellet formulation of claim 20, wherein the enteric coating comprises poly(methacylic acid-co-methyl methacrylate) 1:2 and poly(methacylic acid-co-methyl methacrylate) 1:1.

22. The pellet formulation of claim 18, wherein the matrix-forming polymer makes up at least 1% of the total weight of the core.

23. The pellet formulation of claim 18, wherein the polymer matrix comprises a non gel-forming polymer.

24. The pellet formulation as claimed in claim 18, wherein the pellets have a size of 0.5 to 1 mm.

25. The pellet formulation as claimed in claim 18, wherein the pellet formulation is a capsule.

26. The pellet formulation as claimed in claim 18, wherein the pellet formulation is a tablet.

27. The pellet formulation of claim 18, wherein the polymer matrix is water-insoluble in the intestinal tract.

28. A controlled release pellet formulation, comprising
1) homogeneously dispersed 5-aminosalicylic acid in a core comprising a polymer matrix comprising poly (ethylacrylate, methyl methacrylate) (2:1), wherein the polymer matrix is essentially insoluble in the intestinal tract and permeable to artificial intestinal juice, and wherein the polymer matrix comprises at least 1% by weight of the total weight of the core; and
2) an enteric coating;
wherein, when administered to humans, the mean maximal plasma concentration of the 5-aminosalicylic acid is reached at about 4 hours after administration.

29. The controlled release pellet formulation of claim 28, wherein about 10-30% of the 5-aminosalicyclic acid is released from the formulation in 30 minutes at 37° C. in artificial intestinal juice at a pH of about 6.8.

30. The controlled release pellet formulation of claim 28, wherein, when administered to humans, the mean maximal plasma concentration of acetyl-5-aminosalicylic acid is at about 5 hours after administration.

31. The controlled release pellet formulation of claim 28, wherein, when administered to humans, the ratio of the mean plasma concentration of 5-aminosalicylic acid to the mean plasma concentration of acetyl-5-aminosalicylic acid at about 4 hours after administration is about 1:2.

32. The controlled release pellet formulation of claim 28, wherein, when administered to humans, the ratio of the mean plasma concentration of 5-aminosalicylic acid to the mean plasma concentration of acetyl-5-aminosalicylic acid at about 6 hours after administration is about 1:3.

33. The controlled release pellet formulation of claim 28, wherein, when administered to humans, the ratio of the mean plasma concentration of 5-aminosalicylic acid to the mean plasma concentration of acetyl-5-aminosalicylic acid at about 8 hours after administration is about 1:5.

34. The controlled release pellet formulation of claim 28, wherein, when the controlled release pellet formulation is administered to humans, the mean plasma concentration of 5-aminosalicyclic acid is less than about 1564 ng/ml at about 5 hours after administration.

35. The controlled release pellet formulation of claim 28, wherein, when administered to humans, the mean plasma concentration of 5-aminosalicylic acid is less than about 924 ng/ml at about 6 hours after administration.

36. The controlled release pellet formulation of claim 28, wherein, when the controlled release pellet formulation is administered to humans, the mean plasma concentration of acetyl-5-aminosalicylic acid is less than about 2511 ng/ml at about 5 hours after administration.

37. The controlled release pellet formulation of claim 28, wherein, when administered to humans, the mean plasma concentration of acetyl-5-aminosalicyclic acid is less than about 2243 ng/ml at about 6 hours after administration.

38. A controlled release pellet formulation comprising:
homogeneously dispersed 5-aminosalicyclic acid in a polymer matrix comprising poly (ethylacrylate, methyl methacrylate) (2:1), wherein the polymer matrix is essentially insoluble in the intestinal tract and permeable to intestinal fluid; and
an enteric coating;
wherein, when administered to humans, the average cumulative fecal excretion of 5-aminosalicyclic acid is greater than 250 mg.

39. The controlled release pellet formulation of claim 38, wherein the average cumulative fecal excretion is measured approximately 72 hours after administration.

40. The controlled release pellet formulation of claim 39, wherein the average cumulative fecal excretion of 5-aminosalicyclic acid is greater than 280 mg.

41. The controlled release formulation of claim 40, wherein the polymer matrix comprises at least 1% by weight of the total weight of the core.

42. An orally administrable pharmaceutical pellet formulation having a controlled release profile for the treatment of the intestinal tract, which comprises a core and an enteric coating, the core including aminosalicylic acid or a pharmaceutically acceptable salt thereof, wherein the aminosalicylic acid or pharmaceutically acceptable salt thereof is present in the core and homogenously dispersed in a non gel-forming polymer matrix comprising poly (ethylacrylate, methyl methacrylate) (2:1), wherein the polymer matrix is essentially insoluble in the intestinal tract and permeable to intestinal fluids and the aminosalicylic acid, and wherein the matrix-forming polymer makes up at least 1% and up to approximately 21% by weight of the total weight of the core.

43. The pellet formulation of claim 42, wherein, when administered to humans, the mean maximal plasma concentration of the 5-aminosalicylic acid is reached at about 4 hours after administration.

44. The pellet formulation of claim 42, wherein the pellet formulation is a capsule.

45. The pellet formulation of claim 42, wherein the pellets formulation is a tablet.

46. The pellet formulation of claim 42, wherein the pellets have a size of 0.1 to 3 mm.

47. The pellet formulation of claim 42, wherein the polymer matrix is water-insoluble in the intestinal tract.

48. The pellet formulation of claim 42, wherein, when the controlled release pellet formulation is administered to humans, the mean plasma concentration of 5-aminosalicyclic acid is less than about 1564 ng/ml at about 5 hours after administration.

49. The pellet formulation of claim 42, wherein, when administered to humans, the average cumulative fecal excretion of 5-aminosalicyclic acid is greater than 250 mg.

\* \* \* \* \*